United States Patent
Sandell (10) Patent No.: US 9,555,409 B2
(45) Date of Patent: *Jan. 31, 2017

(54) ROTATABLE SAMPLE DISK AND METHOD OF LOADING A SAMPLE DISK

(75) Inventor: Donald R. Sandell, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 12/545,023

(22) Filed: Aug. 20, 2009

(65) Prior Publication Data

US 2010/0216227 A1    Aug. 26, 2010

Related U.S. Application Data (60) Continuation of application No. 11/484,093, filed on Jul. 11, 2006, now Pat. No. 7,592,172, which is a
(Continued)

(51) Int. Cl.
*C12M 1/38*  (2006.01)
*B01L 3/00*  (2006.01)
(Continued)

(52) U.S. Cl.
CPC ...... *B01L 3/502715* (2013.01); *B01F 13/0059* (2013.01); *B01F 15/0201* (2013.01);
(Continued)

(58) Field of Classification Search
CPC ............. B01F 13/0059; B01F 15/0201; B01F 15/0233; B01L 3/5025; B01L 3/502707; B01L 3/502715; B01L 3/502738; B01L 3/50273; B01L 2200/0642; B01L 2300/0803; B01L 2400/0409; G01N 35/025
(Continued)

(56) References Cited

U.S. PATENT DOCUMENTS

| 4,244,916 A | 1/1981 | Guigan |
| 5,333,675 A | 8/1994 | Mullis et al. |
| (Continued) | | |

FOREIGN PATENT DOCUMENTS

| EP | 0 693 560 A2 | 1/1996 |
| EP | 0693560 | * 1/1996 |
| (Continued) | | |

OTHER PUBLICATIONS

G. Betzl, "Reproducibility of PCR on the LightCycler System," Biochemica No. 1, 2000, pp. 22-26.
(Continued)

*Primary Examiner* — William H Beisner
*Assistant Examiner* — Danielle Henkel (57) ABSTRACT

A rotatable sample disk configured for samples of biological material. The sample disk may include a fill chamber for storing a first biological material, a plurality of first sample chambers positioned in the sample disk farther from the rotational axis of the sample disk than the fill chamber, a plurality of second sample chambers, and a plurality of circumferential fill channels. Each of the second sample chambers may be configured to permit fluid communication with a respective first sample chamber. The plurality of circumferential fill conduits may be configured to permit transfer of the first biological material from the fill chamber to the plurality of first sample chambers upon a first rotation of the sample disk about the rotational axis. Methods of loading a plurality of sample chambers in a sample disk are also provided.

17 Claims, 9 Drawing Sheets

Related U.S. Application Data division of application No. 10/193,680, filed on Jul. 12, 2002, now Pat. No. 7,083,974.

(51) Int. Cl.
  *B01L 7/00* (2006.01)
  *B01F 13/00* (2006.01)
  *B01F 15/02* (2006.01)
  *G01N 35/02* (2006.01)

(52) U.S. Cl.
  CPC ........ *B01F 15/0233* (2013.01); *B01L 3/5025* (2013.01); *B01L 3/50273* (2013.01); *B01L 3/502707* (2013.01); *B01L 3/502738* (2013.01); *B01L 7/52* (2013.01); *G01N 35/025* (2013.01); *B01L 2200/0642* (2013.01); *B01L 2300/0803* (2013.01); *B01L 2400/0409* (2013.01)

(58) Field of Classification Search
  USPC ............................................ 435/288.5, 287.2
  See application file for complete search history.

(56) References Cited

U.S. PATENT DOCUMENTS

| | | |
|---|---|---|
| 5,475,610 A | 12/1995 | Atwood et al. |
| 5,656,493 A | 8/1997 | Mullis et al. |
| 5,693,233 A | 12/1997 | Schembri |
| 5,928,907 A | 7/1999 | Woudenberg et al. |
| 6,015,674 A | 1/2000 | Woudenberg et al. |
| 6,174,670 B1 | 1/2001 | Wittwer et al. |
| 6,303,305 B1 | 10/2001 | Wittwer et al. |
| 6,387,621 B1 | 5/2002 | Wittwer |
| 7,083,974 B2 | 8/2006 | Sandell |
| 7,592,172 B2 | 9/2009 | Sandell |
| 2002/0047003 A1* | 4/2002 | Bedingham et al. ......... 219/388 |

FOREIGN PATENT DOCUMENTS

| | | |
|---|---|---|
| WO | WO 97/21090 | 6/1997 |
| WO | WO 97/36681 | 10/1997 |
| WO | WO 99/60381 | 11/1999 |
| WO | WO 00/79285 A2 | 12/2000 |
| WO | WO 01/28684 A2 | 4/2001 |
| WO | WO 01/35079 A1 | 5/2001 |
| WO | WO 01/87485 A2 | 11/2001 |
| WO | WO 01/87486 A2 | 11/2001 |
| WO | WO 02/00347 A2 | 1/2002 |
| WO | WO 02/01180 A2 | 1/2002 |
| WO | WO 02/01181 A2 | 1/2002 |
| WO | WO 02/074438 A2 | 9/2002 |

OTHER PUBLICATIONS

International Search Report for PCT Application No. PCT/US03/19551, mailed on Nov. 7, 2003.

\* cited by examiner

ROTATABLE SAMPLE DISK AND METHOD OF LOADING A SAMPLE DISK

CROSS REFERENCE TO RELATED APPLICATIONS

This application is a continuation of patent application Ser. No. 11/484,093 filed Jul. 11, 2006, now U.S. Pat. No. 7,592,172, which is a divisional of patent application Ser. No. 10/193,680 filed Jul. 12, 2002, now U.S. Pat. No. 7,083,974, both of which are incorporated herein by reference.

FIELD

The present teachings relate generally to a sample disk configured for samples of biological material, and methods of loading a sample disk. The present teachings further relate, in various aspects, to a sample disk that is rotatable about a rotational axis in order to centrifugally load sample chambers of the sample disk with biological material.

BACKGROUND

Biological testing has become an important tool in detecting and monitoring diseases. In the biological testing field, thermal cycling is used to amplify nucleic acids by, for example, performing polymerase chain reactions (PCR) and other reactions. PCR, for example, has become a valuable research tool with applications such as cloning, analysis of genetic expression, DNA sequencing, and drug discovery. Methods such as PCR may be used to detect a reaction of a test sample to an analyte-specific reagent. Typically, an analyte-specific reagent is placed in each sample chamber in advance of performing the testing. The test sample is then later inserted into the sample chambers, and the sample well tray or microcard is then transported to a thermal cycling device.

Recent developments in the field have led to an increased demand for biological testing devices. Biological testing devices are now being used in an increasing number of ways. It is desirable to provide a more efficient and compact method and structure for filling and thermally cycling substrates such as sample trays and microcards.

In typical systems, the sample tray or microcard is loaded with reagent, then loaded with the test sample, and then transported and inserted into a separate device for thermal cycling. It is desirable to reduce the amount of time and number of steps taken to fill and thermally cycle a sample tray or microcard.

SUMMARY

Various aspects generally relate to, among other things, a rotatable sample disk configured for samples of biological material. According to one various aspects, the sample disk can include a fill chamber for storing a first biological material, a plurality of first sample chambers positioned in the sample disk farther from a rotational axis than the fill chamber, a plurality of second sample chambers, and a plurality of circumferential fill conduits positioned adjacent the plurality of first sample chambers. In various embodiments, the fill chamber is configured for rotation on the sample disk about a rotational axis. Each of the second sample chambers may be configured to permit fluid communication with a respective first sample chamber. The second sample chambers may be positioned closer to the rotational axis than the first sample chambers. The plurality of circumferential fill channels may be configured to permit transfer of the first biological material from the fill chamber to the plurality of first sample chambers upon a first rotation of the sample disk about the rotational axis.

Various aspects comprise a method of loading a plurality of sample chambers on a sample disk. The method can include the step of providing a sample disk with a fill chamber, a plurality of first sample chambers, and a plurality of second sample chambers. The method may further comprise loading the plurality of first sample chambers with a first biological material by rotating the sample disk about a rotational axis so that a first biological material in the fill chamber travels through a plurality of circumferential fill conduits connecting the fill chamber with the first sample chambers. The plurality of circumferential fill conduits may be positioned between adjacent first sample chambers. The method may further comprise providing a plurality of second sample chambers with a second biological material, and transporting the second biological material from the second sample chambers into the first sample chambers by rotating the sample disk about the rotational axis so that the second biological material passes from the second sample chambers through a plurality of radial fill conduits into the first sample chambers.

Various aspects comprise an apparatus for centrifugally loading and thermally cycling a sample disk. The apparatus can comprise a sample disk having a plurality of first sample chambers, a plurality of second sample chambers, and a reservoir for storing a volume of liquid sample. The apparatus may further include means for centrifugally loading the plurality of first sample chambers with liquid sample upon rotation of the sample disk about a rotational axis of the sample disk. The apparatus may further includes means for centrifugally loading the plurality of first sample chambers with a biological material from the plurality of second sample chamber. The apparatus may further include a means for thermally cycling the plurality of first sample chambers of the sample disk.

Various other aspects comprise an apparatus configured for containing samples of biological material during a thermal cycling operation. The apparatus may include a microcard configured for rotation about a rotational axis, a plurality of first sample chambers positioned on the microcard around the rotational axis, and a plurality of second sample chambers positioned in the microcard around the rotational axis. The second sample chambers may be positioned closer to the rotational axis than the first sample chambers. The apparatus may further comprise a plurality of channels formed in the microcard. The plurality of channels may comprise a plurality of circumferential channels and a plurality of radial channels. The circumferential channels may be positioned between adjacent first sample chambers to transport a first biological material from a reservoir into the plurality of first sample chambers upon rotation of the microcard about the rotational axis. The plurality of radial channels may be positioned between corresponding first and second sample chambers to transport a second biological material from the second sample chambers to the first sample chambers upon a further rotation of the microcard about the rotational axis. The plurality of first sample chambers may be configured to permit optical detection of the biological materials in the first sample chambers.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate several exemplary embodiments. In the drawings.

DETAILED DESCRIPTION OF THE PRESENT INVENTION

Reference will now be made to various exemplary embodiments, examples of which are illustrated in the accompanying drawings. Wherever possible, the same reference numbers are used in the drawings and the description to refer to the same or like parts.

In accordance with various embodiments, a rotatable sample disk configured for samples of biological material is provided. In one aspect, the sample disk includes a fill chamber for storing a first biological material, a plurality of first sample chambers positioned in the sample disk, a plurality of second sample disks, and a plurality of conduits configured to permit transfer of the first biological material from the fill chamber to the plurality of first sample chambers upon a first rotation of the sample disk about a rotational axis of the sample disk.

Although terms like "horizontal," "vertical," "upward," "downward," "radial," and "axial" are used in describing various aspects of the present teachings, it should be understood that such terms are for purposes of more easily describing the teachings, and do not limit the scope of the teachings.

In various embodiments, such as illustrated in FIGS. 1-2, a sample disk 10 is provided. The sample disk 10 may be configured for thermally cycling samples of biological material in a thermal cycling device. The thermal cycling device may be configured to perform nucleic acid amplification on samples of biological material. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In various embodiments, the sample disk may be used in a thermal cycling device that performs real-time detection of the nucleic acid amplification of the samples in the sample disk during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification process. Alternatively, the sample disk may be used in a thermal cycling device that performs endpoint detection of the nucleic acid amplification of the samples. One type of detection apparatus that may be used with the present teachings for either real-time or endpoint detection is the LightCycler™ Instrument manufactured by Roche Molecular Biochemicals. Another type of detection apparatus includes a single LED sensor for detecting the characteristics of the samples as the sample disk rotates about a rotational axis. Several other types of detection apparatus are shown in WO 02/00347A2 to Bedingham et al., the complete disclosure of which is hereby incorporated by reference for any purpose.

Figure 4:
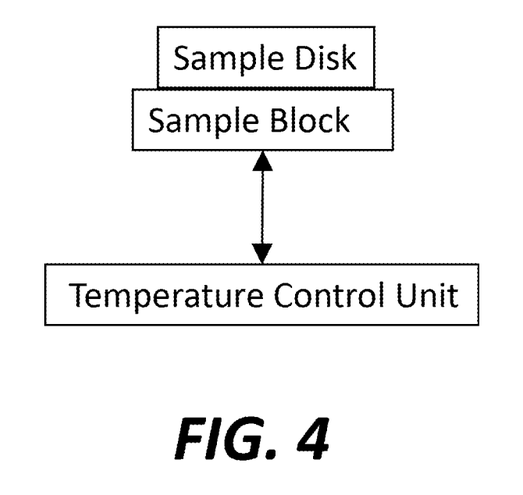
FIG. 4 is a flowchart according to another embodiment of the present teachings, depicting the relationship between a sample disk, a sample block and a temperature control unit.

Referring to FIG. 4, the sample disk may be configured to contact a sample block for thermally cycling the biological materials in the sample chambers of the sample disk. The sample block may be operatively connected to a temperature control unit programmed to raise and lower the temperature of the sample block according to a user-defined profile. For example, in various embodiments, a user may supply data defining time and temperature parameters of the desired PCR protocol to a control computer that causes a central processing unit (CPU) of the temperature control unit to control thermal cycling of the sample block. Several non-limiting examples of suitable temperature control units for raising and lowering the temperature of a sample block for a microcard or other sample-holding member are described in U.S. Pat. No. 5,656,493 to Mullis et al. and U.S. Pat. No. 5,475,610 to Atwood et al., the disclosures of which are both hereby incorporated by reference for any purpose.

In one embodiment, the rotatable sample disk comprises at least one fill chamber on the rotatable sample disk, a plurality of first sample chambers, a plurality of second sample chambers, and a plurality of fill conduits. One embodiment of a sample disk of the present teachings is shown in FIGS. 1-2. As embodied herein and shown in FIGS. 1-2, the rotatable sample disk is a microcard or sample tray generally designated by reference number 10. The sample disk is generally rotatable about a rotational axis 12. The rotatable sample disk 10 is shown as being a circular plate, however, it is understood that the sample disk may be any other suitable shape such as rectangular or square. A circular shape is shown merely because a circular shape will typically minimize the amount of space taken up by the sample disk as it rotates about rotational axis 12.

Figure 1A:
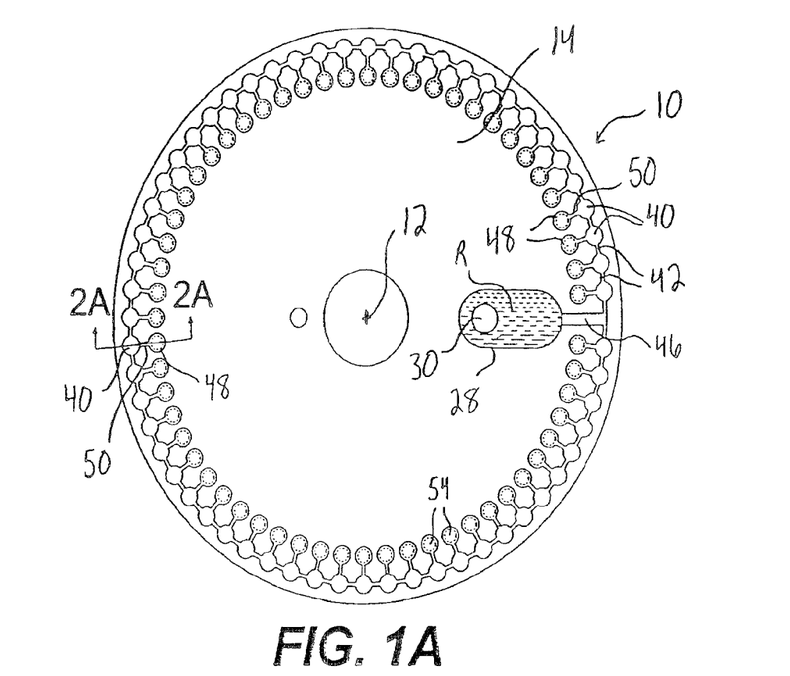
FIG. 1A is a plan view of an exemplary embodiment of a sample disk according to the present teachings, prior to spinning the disk, with a first biological material in a fill chamber.
Figure 1B:
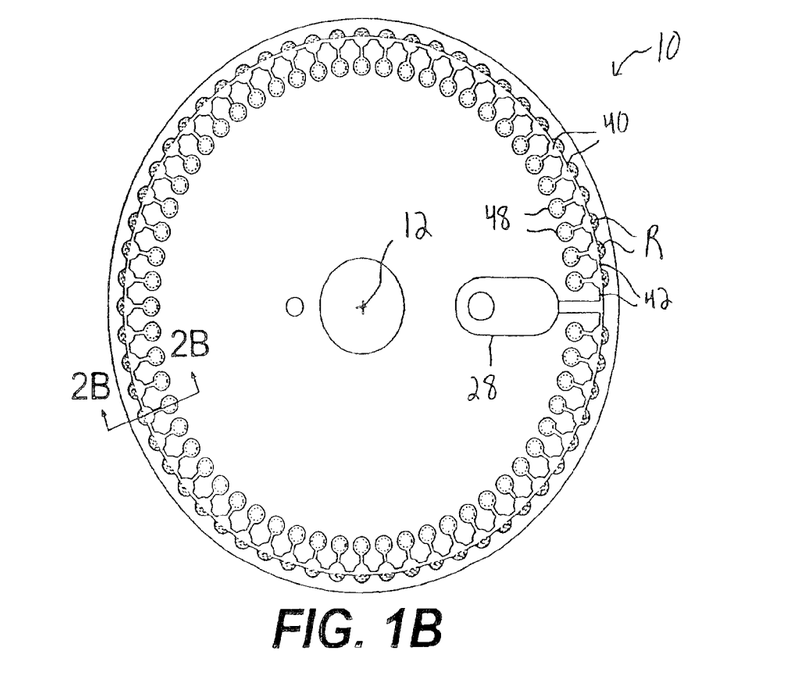
FIG. 1B is a plan view of the sample disk of FIG. 1A after centrifugal loading of the first biological material into outer sample chambers of the disk.
Figure 1C:
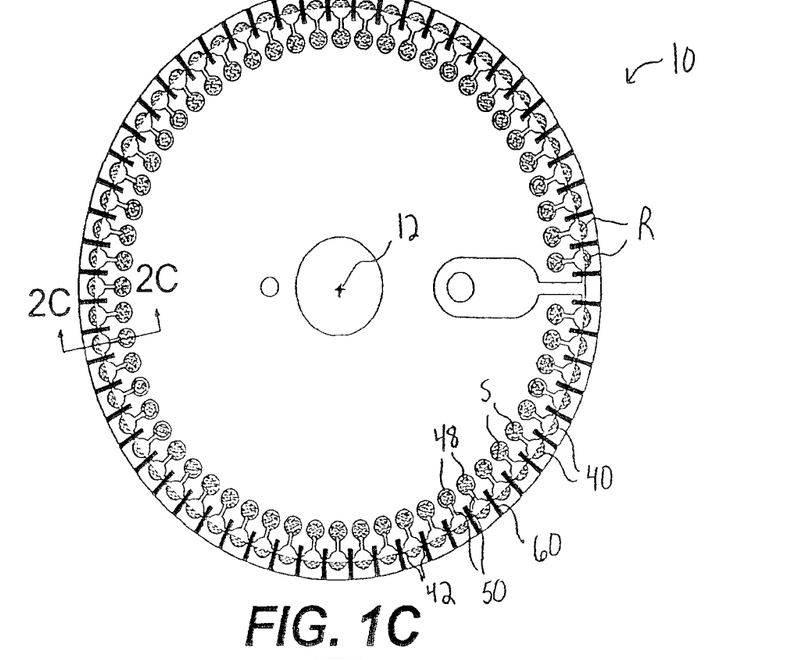
FIG. 1C is a plan view of the sample disk of FIG. 1B, with a second biological material such as a test sample in inner sample chambers of the disk and with circumferential fill conduits being in a blocked state.
Figure 1D:
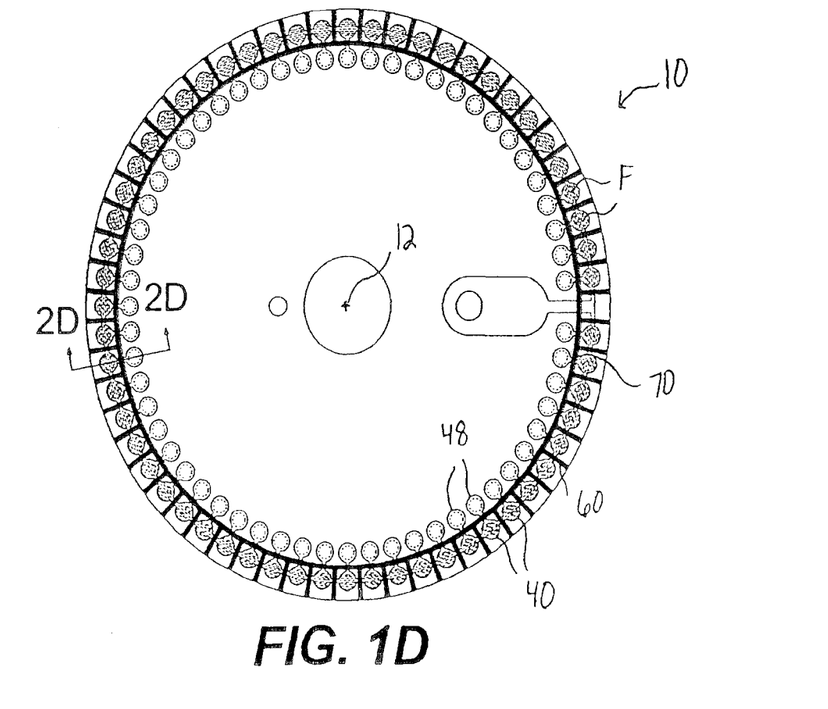
FIG. 1D is a plan view of the sample disk of FIG. 1C after a second centrifugal loading operation, and with the circumferential fill conduits and radial fill conduits in a blocked state.
Figure 2A:
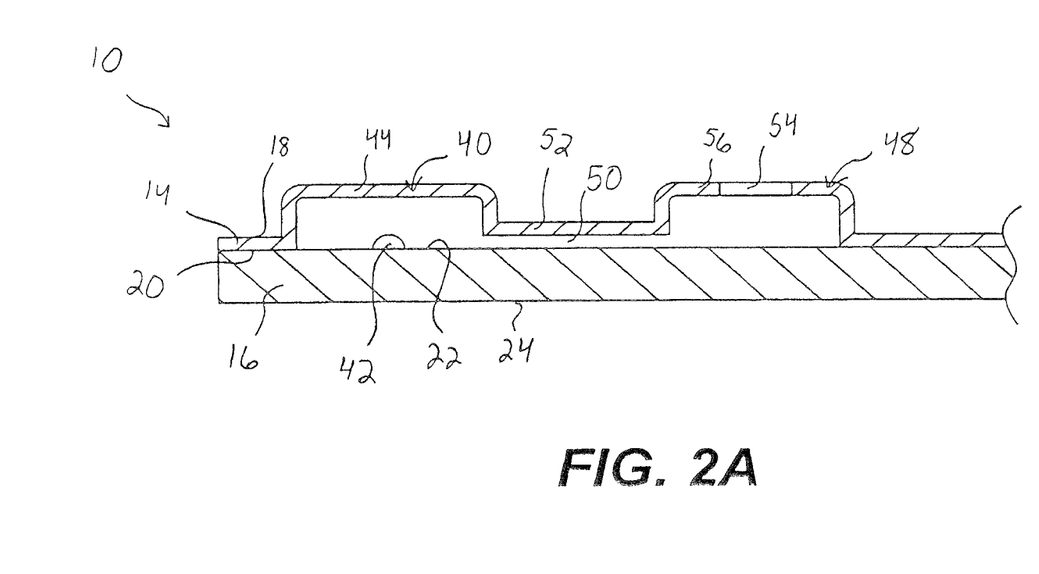
FIG. 2A is a cross-sectional view along line 2A-2A of FIG. 1A.

As shown in FIGS. 1-2, particularly FIG. 2A, the rotatable sample disk may include a first layer 14 and second layer 16. For purposes of convenience, the first layer may be referred to as the "top layer" and the second layer may be referred to as the "bottom layer." As shown for example in FIG. 2A, the first layer 14 includes a top surface 18 and bottom surface 20. The second layer 16 generally includes a top surface 22 and a bottom surface 24. The first and second layers may be made out of any suitable material or materials. In a typical embodiment, the first layer 14 is made of a polymeric material such as polypropylene and the second layer 16 is made out of a metal such as metal foil. Alternatively, both the first layer 14 and the second layer 16 may be made out of a polymeric material. In another embodiment, the first layer is made out of polypropylene and the second layer is made out of lexan. Other suitable polymers include polyester, polycarbonate, and polyethylene.

In the embodiment shown, the first layer 14 includes all of the features of the sample chambers, fill conduits, and fill chambers in a polymeric sheet that has been molded, vacuum formed, pressure formed, compression molded, or otherwise processed. The second layer 16 is provided as a substantially flat plate that is attached to the first layer 14 to complete formation of the features of the sample chambers, fill conduits, and fill conduits. It should be understood that the features may be provided in both layers of the sample disk. It may be desired that the first and second layer are made out of PCR-compatible materials. It may also be desirable that the materials selected for the first and second layer exhibit good water barrier properties.

A variety of methods of forming the layers and methods of adhering the two layers together are described in, for example, WO 02/01180A2 to Bedingham et al., the complete disclosure of which is hereby incorporated by reference for any purpose, and WO 02/00347A2 to Bedingham et al., incorporated herein above. The structure of the first and second layers will be described in greater detail below, as the structure of the first and second layers define the sample chambers, fill chambers, and fill conduits that comprise sample disk 10.

In various embodiments, the sample disk includes at least one fill chamber for storing a first biological material, and a plurality of first sample chambers. As embodied herein and shown in FIGS. 1A-1D, the sample disk includes a fill chamber 28 positioned on the upper layer 14 of the sample disk, and a plurality of first sample chambers 40 (also referred to as "outer sample chambers"). The fill chamber of one embodiment of the present teachings serves as a reservoir for storing the first biological material prior to the sample disk being rotated to centrifugally load the first biological material into the outer sample chambers.

In the embodiment shown in FIGS. 1-2, the first biological material would typically be a reagent, particularly an analyte-specific reagent. Analyte-specific reagents are well-known in the art. It should be understood that the first biological material may be any other type of suitable biological material, such as a test sample material, instead of a reagent. For purposes of conveniently describing the embodiment of FIGS. 1-2, the first biological material will be described as a reagent. In the embodiment shown in FIGS. 1-2, the user can select an appropriate reagent or other biological material, thereby providing more flexibility compared to testing devices in which the reagents are pre-programmed into the testing device. If the sample disk provides for a single "primary" fill chamber 28, one reagent may be used in a single sample disk.

The fill chamber may have any type of shape suitable for storing a liquid. In the example shown in FIGS. 1A-1D, the fill chamber 28 is shown as being generally oval, however any other suitable shape is acceptable. The volume of the fill chamber can range from quite large to very small, depending on the desired amount of reagent (or other first biological material) for each of the outer sample chambers 40 into which it will be centrifugally loaded in a manner described below. Typically, the total amount of reagent placed in the fill chamber will be predetermined prior to entry of the reagent into the fill chamber 28. The amount of volume may be calculated based on the amount of reagent desired in each sample chamber, multiplied by the total number of sample chambers on the sample disk. By way of example only, in an embodiment in which there are seventy-two sample chambers 28, the predetermined amount of reagent to be inserted into the fill chamber 28 may be seventy-two times the amount of reagent desired in each outer sample chamber. For example, in a scenario in which it is desired that each of the seventy-two outer sample chambers eventually contain approximately 5 μl of reagent, then the approximate total volume of the fill chamber would be approximately 360 μl. The desired amount of reagent can greatly vary however, depending on a large number of factors.

In various embodiments, the fill chamber may include an orifice for permitting loading of the first biological material into the fill chamber. As shown in FIGS. 1A-1D, orifice 30 may be provided on the outside of the fill chamber 28. The orifice 30 is typically sized in order to permit pipetting of the first biological material, such as a reagent, into the fill chamber. Alternatively, the fill chamber may be filled by any other acceptable method for inserting a first biological material such as a reagent into a reservoir. It should be understood that although the drawings only illustrate a single fill chamber 28, it is easily understood that the sample disk could have any number of "primary" fill chambers. The fill chambers could be positioned around the rotational axis, typically in a concentric and evenly spaced manner in order to promote a uniform distribution of the first biological material into the sample chambers.

In various embodiments, the sample disk includes a plurality of first sample chambers, a plurality of second sample chambers, and a plurality of fill conduits. In the embodiment shown in FIGS. 1-2, the sample disk includes a plurality of first sample chambers (or "outer sample chambers") 40 and a plurality of second sample chambers (or "inner sample chambers") 48. As shown for example in FIG. 1A, the plurality of outer sample chambers 40 are positioned concentrically about the rotational axis of the 12. It is also contemplated that the outer sample chambers may be positioned non-concentrically, however it is typically desired to have the outer sample chambers positioned concentrically to enhance uniform volumes of biological material in each of the outer sample chambers. The outer sample chambers 40 may be equally spaced from one another as shown in FIGS. 1A and 1B, or the spacing may be varied.

The sample chambers may have any shape suitable for thermal cycling. In the embodiment shown in FIGS. 1-2, the outer sample chambers 40 are cylindrical with flat top surface 44, however, any other known shape is also suitable. In a typical system, light may be transmitted through the top surface of the outer sample chambers during detection of the characteristics of the biological material in the sample chamber. As best seen in FIG. 2A, outer sample chamber 40 is formed by a raised flat top surface 44 of first layer 14 that creates a space between the first layer and the top surface 22 of second layer 16. The raised flat top surface 44 may be formed by any known method. The outer sample chamber 40 defines a volume for storing biological materials.

In the embodiment shown in FIG. 1A, a total of seventy-two (72) outer sample chambers are included on the sample disk, however it is possible to use anywhere from one to at least several thousand outer sample chambers. The outer sample chambers are preferably configured to be PCR-compatible, and typically have a surface such as top surface 44 through which an optical detection system (not shown) can detect the characteristics of sample materials stored in the sample chambers. The concept of sample chambers is known in the art. In a more typical embodiment, the size of the sample chambers may vary from 0.1 μl to several thousand μl. In a more typical embodiment such as shown in FIG. 1, the outer sample chambers 40 are configured to have a volume of approximately 10 μl. It should be understood that this volume is for purposes of example only. In some instances, it may be desirable to have smaller volumes in order to reduce the amount of reagent and sample material required to load the sample disk. In other instances, it may be desirable to have a greater volume. In various embodiments, the chambers are configured to hold no greater than 1,000 μl. In other embodiments, the chambers are configured to hold no more than 200 μl, no more than 100 μl, no more than 50 μl, or no more than 0.5 μl.

In accordance with various embodiments, the sample disk includes a plurality of fill conduits configured to permit transfer of a first biological material from the fill chamber to the plurality of first sample chambers upon rotation of the sample disk about the rotational axis. As embodied herein and shown in FIGS. 1A and 1B, the plurality of fill conduits includes a plurality of circumferential fill conduits 42 positioned between adjacent outer sample chambers 40. In the embodiment shown in FIG. 1A, the circumferential fill conduits 42 are positioned concentrically about the rotational axis 12 at a fixed diameter. It should be understood that the circumferential fill conduits do not necessarily need to be concentrically spaced from the rotational axis 12. In FIGS. 1A and 1B, the circumferential fill conduits 42 are shown bisecting the center of the sides of each of the outer sample chambers 40. The circumferential fill conduits are designed to permit fluid communication between adjacent outer sample chambers. In the embodiment shown, the circumferential fill conduits 42 are defined by features formed in the first layer 14 that create a space with the top surface 22 of the second layer 16. The features in the first layer may be formed by any known processing method such as, but not limited to, molding, vacuum forming, pressure forming, and compression molding. In various embodiments, the fill conduits (or channels) described herein may have a range of sizes. In various embodiments, such conduits have at least one cross-sectional dimension, e.g., width, depth, or diameter, of between 1 to 750 micrometers. In various other embodiments, such conduits have at least one cross-sectional dimension of from between 10 to 500 micrometers, or from between 50 to 250 micrometers.

In various embodiments, the sample disk comprises a primary fill conduit extending from the fill chamber to the circumferential fill conduits and/or outer sample chambers. As shown in FIGS. 1A-1D, a primary fill conduit 46 may extend between the fill chamber 28 to one of the circumferential fill conduits 42. In one embodiment, the primary fill conduit 46 extends radially in order to transport the reagent in the fill chamber to the circumferential fill conduit 42 upon rotation of the sample disk about rotational axis 12. The primary fill conduit may be sized to prevent the first biological material, typically reagent R, from passing through it while the sample disk is stationary. If the primary fill conduits are an appropriate size and shape, the surface tension of the interior surface of the conduit will prevent the flow of the reagent through the primary fill conduit when the sample disk is at a resting position (or rotating at a speed below a predetermined speed at which the reagent will begin to flow due to centrifugal force).

It should be understood that the primary fill conduit need not be completely radial in order to transport the reagent. Likewise, it should also be understood that, in some embodiments, the primary fill conduit could be eliminated by moving the fill chamber closer to or adjacent the circumferential fill conduit. Although only one primary fill conduit 46 is shown in FIGS. 1A-1D, it is contemplated that several fill conduits could be used, particularly in embodiments having a plurality of fill chambers. For example, it is conceivable to have the same number of fill chambers as outer sample chambers. In such an embodiment, each fill chamber may have an individual primary fill conduit. With an embodiment having seventy-two outer sample chambers, a total of seventy-two fill chambers and seventy-two primary fill conduits might be provided. It is of course contemplated that a smaller number of fill chambers and primary fill conduits could also be used.

It should also be understood that several sets of fill chambers and outer sample chambers may be provided. In one embodiment, each set of fill chambers and one or more sample chambers could use separate samples to be tested. This would allow for a large amount of samples to be tested on a single sample disk. In another embodiment, each fill chamber could be ganged with one or more outer sample chambers. It should also be understood that a plurality of disks could be stacked together.

Figure 2B:
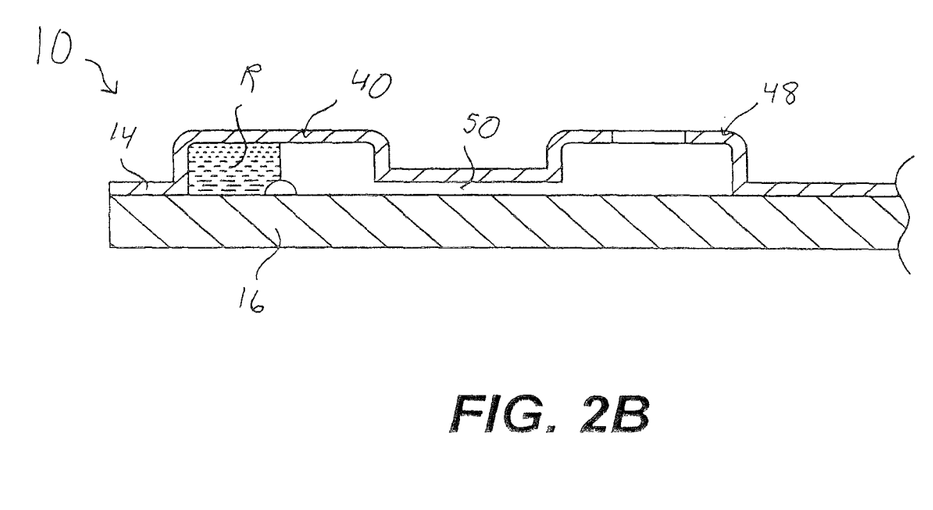
FIG. 2B is a cross-sectional view along line 2B-2B of FIG. 1B.

The sample disk may further include a plurality of inner sample chambers positioned radially inside of the outer sample chambers. In the embodiment shown for example in FIGS. 1A and 2A, the inner sample chambers 48 are similar in shape to the outer sample chambers 40. The inner sample chambers 48 however may have any shape suitable for storing a second biological material. Inner sample chambers 48 may be positioned closer to the rotational axis 12 than the outer sample chambers 40, i.e., radially inside of the outer sample chambers. In the embodiment shown in FIGS. 1-2, the inner sample chambers 48 may be used to store a second biological material, typically the sample material to be tested, after a first biological material such as a reagent has been centrifugally loaded from the fill chamber to the outer sample chambers 40. After the reagent has been centrifugally loaded into the outer sample chambers as shown in FIGS. 1B and 2B, the inner sample chambers 48 may be filled with a sample to be tested.

As shown in FIG. 1A, in a typical arrangement, an equal number of inner sample chambers and outer sample chambers are provided. In the example shown in FIG. 1A, the sample disk includes seventy-two inner sample chambers 48 and seventy-two outer sample chambers 40. It is understood that any other number of inner sample chambers may be provided. In the embodiment shown, the inner sample chambers 48 are approximately the same size as the outer sample chambers 40, however this can be varied depending on the specific application. For example, in a sample disk configuration in which it is desired to use a large amounts of reagent and a small amount of test sample material, it may be desired to have inner sample chambers that are smaller than the outer sample chambers. Likewise, in the situation where it is not desired to completely fill the outer sample chambers, it may also be desired to have inner sample chambers that are smaller than the outer sample chambers.

In accordance with various embodiments, radial fill conduits may be provided between the second sample chambers and the first sample chambers. In the embodiment shown in FIG. 1, the second or inner sample chambers 48 and first or outer sample chambers 40 are connected by radial fill conduits 50. As shown in FIG. 1A, radial fill conduit 50 extends in a radial direction with respect to rotational axis 12. FIG. 2A illustrates a cross-section along line 2A-2A of FIG. 1A which passes through radial fill conduit 50. As can be seen in FIG. 2A, radial fill conduit is configured to permit fluid communication between the inner sample chamber 48 and outer sample chamber 40. The radial fill conduit is defined by a raised portion 52 in the first layer 14 of the sample disk, and a top surface 22 of the second layer 16 of the sample disk. The raised portion is formed in the first layer 14 by any known method. The radial fill conduits are typically sized in depth so that fluid only passes through the conduit upon a centrifugual force being imparted on the sample disk.

The radial fill conduits 50 are shown having approximately the same size as the circumferential fill conduits 42, however the size and shape of the radial fill conduits may be varied. As will be described later, the radial fill conduits permit transfer of a second biological material from the inner sample chambers 48 to the outer sample chambers 40 upon rotation of the sample disk. In the embodiment described herein, the loading of the second biological material, e.g., sample to be tested, into the outer sample chambers typically occurs after the first biological material, e.g., reagent, has already been pre-loaded into the outer sample chambers. This will be discussed in greater detail in the description of the operation of the sample disk.

In various embodiments, the inner sample chambers 48 may include an orifice for permitting loading of the second biological material into the inner sample chamber. As shown in FIGS. 1A and 2A, for example, an orifice 54 may be formed in the top surface 56 of inner sample chamber 48. The orifice allows for manual or automatic loading of the second biological material, typically the sample test material, into the inner sample chamber 48. A typical method of loading the sample test material is pipetting. Other methods may also be utilized however. Instead of an orifice, any other known type of structure for permitting entry of a liquid into a reservoir may also be used.

In various embodiments, a means for selectively blocking the passage of the first biological material through the circumferential fill conduits is provided. The blocking of the passage of the first biological material, typically a reagent, through the circumferential fill conduits is particularly useful after the reagent has already been centrifugally loaded from the primary fill conduit into the outer sample chambers. The blocking assists in preventing cross-contamination between adjacent outer sample chambers. In the embodiment shown in FIG. 1C, the first layer 14 of the sample disk may be physically deformed at position 60 by a staking device in order to block or occlude the circumferential fill conduits 42. The staking device may be any device that is configured for physically deforming the circumferential fill conduit, such as a knife edge. Alternatively, the second layer 16 may be physically deformed in order to block or occlude the circumferential fill conduits. The materials of the sample disk are typically selected so that staking may effectively occur.

It should be understood, however, that the complete sealing or occluding of the circumferential fill conduits may not be required. For example, it may only be required that the deformation restrict flow, migration or diffusion through a conduit or fluid passageway sufficient to provide the desired isolation of adjacent outer sample chambers. As used in connection with the present teachings, "blocking" or "occlusion" or "closing" will include both partial blocking and complete blocking.

In order to promote more effective blocking, it may be desired to use any other known means for blocking a conduit. For example, it may be useful to use adhesives on either or both of the first and second layer in order to promote sealing of the conduit after the layers are deformed. Instead of physical deformation, the means for blocking may also comprise any other type of melting, bonding, and welding in order to block off the circumferential fill conduit. A number of suitable methods of blocking or occluding a conduit of a microcard are described in WO 02/01180A2 to Bedingham et al., incorporated by reference above.

In various embodiments, a means for selectively blocking the passage of the first and second biological material from the outer sample chambers to the inner sample chambers is provided. The means for blocking is utilized after the biological sample material to be tested, shown as S in FIG. 1C, has been centrifugally loaded from the inner sample chambers 48 into the outer sample chambers 40. When the sample to be tested is centrifugally loaded into the outer sample chamber 40 it mixes with the reagent, shown as R, which was previously loaded into the outer sample chambers 40 as shown in FIGS. 1B and 2B. After the sample to be tested is loaded into the outer sample chambers, it is desired maintain the sample and reagent in the outer sample chambers. A number of different methods and structures may be used to block the radial fill conduits in order to maintain the sample and reagent in the outer sample chambers.

Figure 2C:
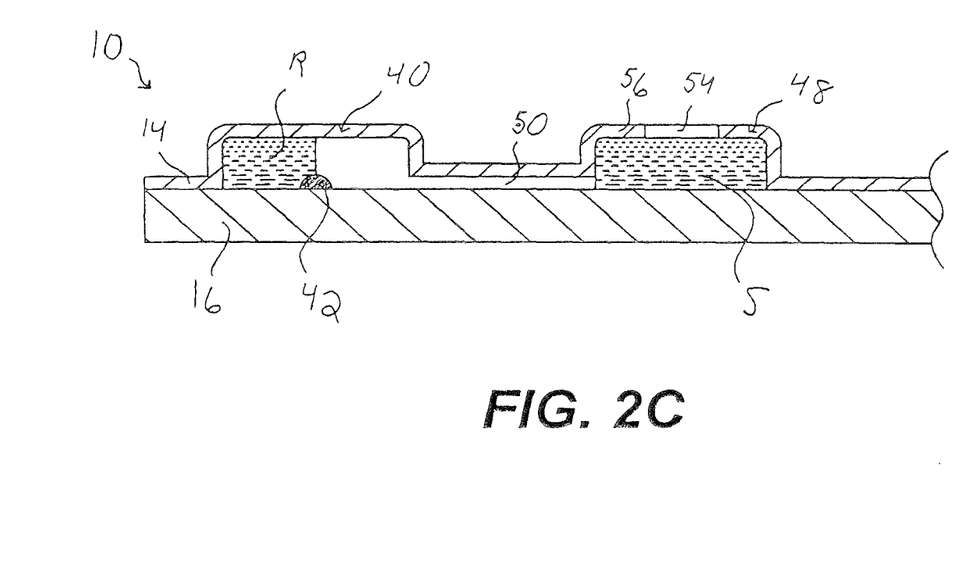
FIG. 2C is a cross-sectional view along line 2C-2C of FIG. 1C.
Figure 2D:
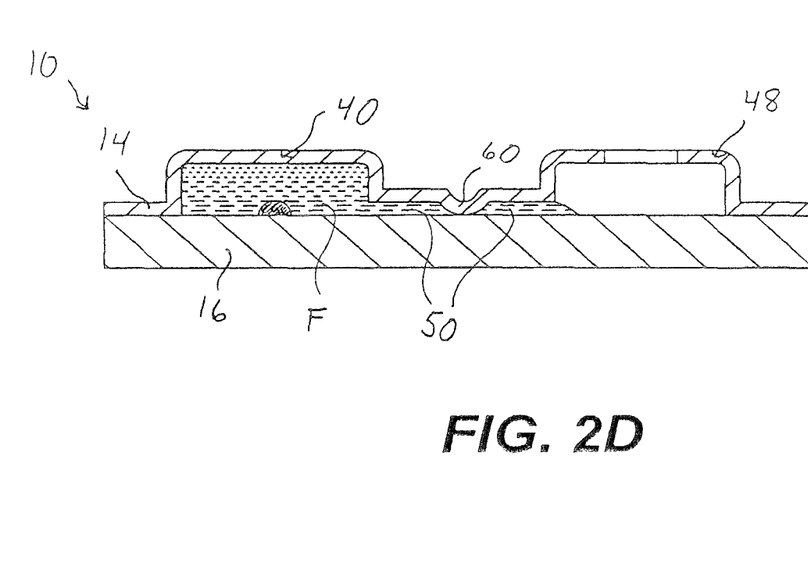
FIG. 2D is a cross-sectional view along line 2D-2D of FIG. 1D.

For example, FIGS. 1D and 2D show an embodiment in which the first layer 14 of the sample disk is physically deformed at position 70 by a staking device, such as a knife edge, in order to block passage of the liquids out of the outer sample chambers. FIG. 2D shows the physically deformed portion 70 of the first layer 14 that has been pressed downward by a staking apparatus in order to block or occlude the passage of liquid through radial fill conduit 50. This blocking is useful so that a constant volume of material is maintained in each of the outer sample chambers 40 during thermal cycling and detection of the sample chambers. This will be discussed in greater detail in the description of the operation of the sample disk.

An example of the operation of the sample disk for the embodiment of FIGS. 1-2 is described below. In the first step of the operation, a sample disk is provided. As shown in FIG. 1A, the sample disk 10 of one embodiment includes, among other things, a fill chamber 28, a primary fill conduit 46, a plurality of outer sample chambers 40, a plurality of inner sample chambers 48, a plurality of circumferential fill conduits 42, and a plurality of radial fill conduits 50. The sample disk 10 is typically placed on the drive shaft of a centrifuge in a thermal cycling device (not shown) so that the sample disk may rotate about rotational axis 12.

Next, a first biological material may be loaded into the fill chamber 28 positioned on the sample disk. As previously discussed, the first biological material in the embodiment of FIGS. 1-2 is typically a reagent. For the sake of ease of discussion, the first biological material will be referred to as a reagent. It should be understood however, that the first biological material may instead be the sample to be tested.

The reagent is labeled R in FIG. 1A. The reagent may be loaded into the fill chamber 30 by any suitable method. One method is to pipette the reagent through orifice 30 positioned on top of the fill chamber 28. In the position shown in FIG. 1A, the reagent fills the fill chamber 28 but does not pass along the primary fill conduit 46 due to the surface tension of the reagent on the primary fill conduit. As shown in FIG. 2A, the outside sample chamber 40 and inner sample chamber 48 are initially empty.

After a predetermined amount of reagent has been loaded into the fill chamber 28, the sample disk 10 is rotated about the rotational axis by the centrifuge (not shown). Upon reaching a certain rotational speed, the centrifugal force will cause the reagent R to flow through the primary fill conduit 46 and through the circumferential fill conduits 42 into the outer sample chambers 40 until the reagent is evenly distributed throughout the outer sample chambers as shown in FIGS. 1B and 2B. In one exemplary embodiment, the reagent fills approximately half of each outer sample chamber, as shown in FIGS. 1B and 2B. Because of the centrifugal force, the reagent will fill the half of the outer sample chamber farthest from rotational axis 12. It should be understood that a greater amount of reagent may be used. A smaller amount of reagent may also be used. If a smaller amount of reagent is used, the sample disk may be modified so that the circumferential fill conduits 42 are positioned farther from the rotational axis 12 than shown in FIGS. 1-2. The circumferential fill channels would be moved closer to the outer edge of the outer sample chambers 40.

It should of course be understood that the centrifugal force to cause loading of the outer sample chambers may be created by any number of rotations, including less than a full rotation.

The circumferential fill conduits 42 shown in FIGS. 1-2 may now be staked by any known method such as physical deformation of the first layer 14 of the sample block to occlude the passage of fluid through the circumferential fill conduits 42. FIGS. 1C and 2C show the circumferential fill conduits 42 being staked at position 60 to prevent fluid communication between adjacent outer sample chambers 40.

After the circumferential fill conduits 42 have been staked, a second biological material, typically a sample S to be tested, may be loaded into the inner sample chambers 48. It should be understood that the second biological material may instead be a reagent or other type of biological material. In one embodiment, the test sample S is inserted into some, if not all, of inner sample chambers 48 shown in FIGS. 1C and 2C through orifice 54 on the top surface 56 of the inner sample chamber 48. The surface tension of the sample prevents the sample from initially flowing through the radial fill conduit 50 into the outer sample chamber 40.

After the sample S has been loaded into the inner sample chambers 48, and the circumferential fill conduits 42 have been staked, both as shown in FIGS. 1C and 2C, the sample disk is rotated again about the rotational axis 12. Upon rotation of the sample disk at a certain speed, the sample S to be tested will be urged by centrifugal force to flow from the inner sample chambers 48 through the radial fill conduits 50 into the outer sample chambers 40. The sample to be tested flows into the outer sample chambers 40 and mixes with the reagent R to form a final test material labeled F in FIGS. 1D and 2D. After the sample to be tested has been loaded into the outer sample chambers, the radial fill conduits 50 are staked to maintain the final test material F (comprising the reagent and the sample to be tested) in the outer sample chambers 40. As shown in FIG. 2D, the radial fill conduit may be staked, in one embodiment, by physically deforming a portion of the top surface of the first layer 14 in a region intersecting the radial fill conduit. The portion of the top surface that is deformed is labeled as reference number 70 in FIG. 2D. After the radial fill conduit is sufficiently blocked, the sample disk may be further rotated and thermally cycled.

During rotation and thermal cycling of the sample block, in one embodiment, the optical characteristics of the final sample F can be detected by an optical detection system. In one embodiment, the optical detection system is similar to the LightCycler™ system of Roche.

In this embodiment, the sample disk may be maintained about a single rotational axis for the processes of filling the sample chambers, thermally cycling the samples, and optically detecting the samples. By such an operation, the cost and time spent loading the sample chambers and thermally cycling the sample chambers may be minimized. Moreover, by providing a sample disk that can be loaded by rotating about a single rotational axis, it is possible to provide an integrated centrifuge and thermal cycling device. Such an integrated centrifuge and thermal cycling device could conceivably be a portable apparatus that can be useful for point of service analysis.

As is clear from the above description, the present teachings include methods of centrifugally loading a plurality of sample chambers in a sample disk. The method may comprise providing a sample. An apparatus for centrifugally loading and thermally cycling a sample disk, comprising: a sample disk having a plurality of first sample chambers, a plurality of second sample chambers, and a reservoir for storing a volume of liquid sample; means for centrifugally loading the plurality of first sample chamber with liquid sample upon rotation of the sample disk about a rotational axis of the sample disk; and means for centrifugally loading the plurality of first sample chambers with a biological material from the plurality of second sample chambers; and means for thermally cycling the plurality of first sample chambers of the sample disk.

Figure 3A:
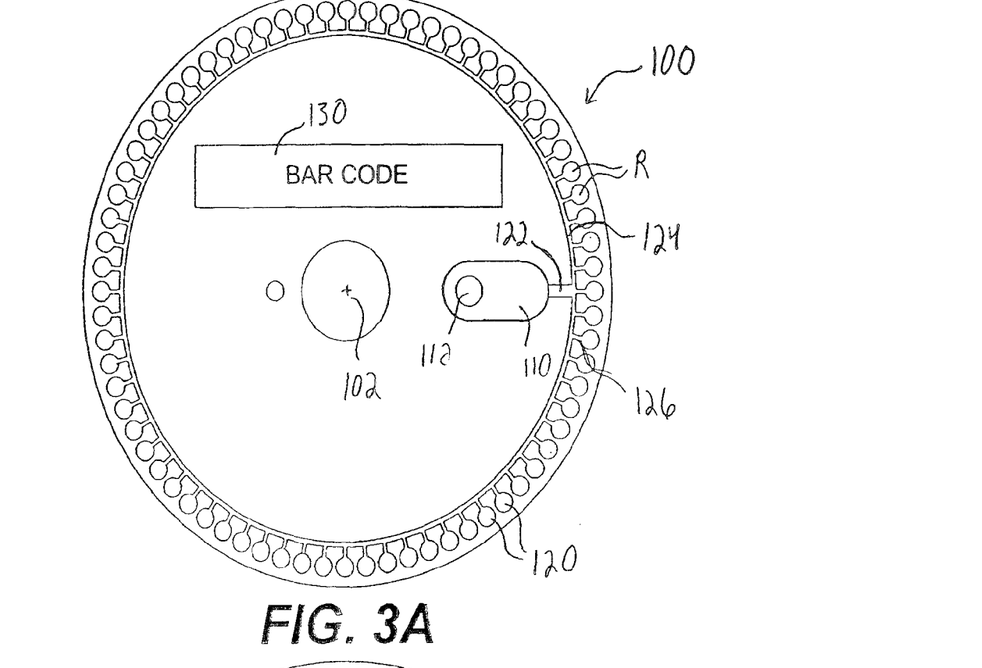
FIG. 3A is a plan view of a sample disk according to another embodiment of the present teachings, prior to filling a fill chamber with a test sample material.
Figure 3B:
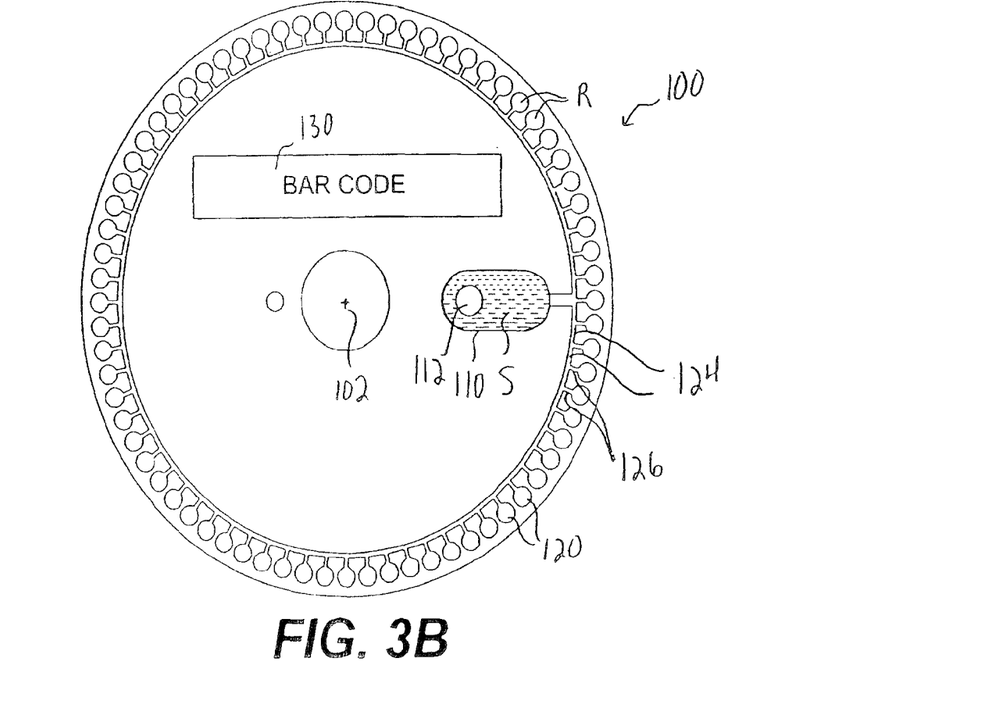
FIG. 3B is a plan view of the sample disk of FIG. 3A after filling the fill chamber with a test sample material.
Figure 3C:
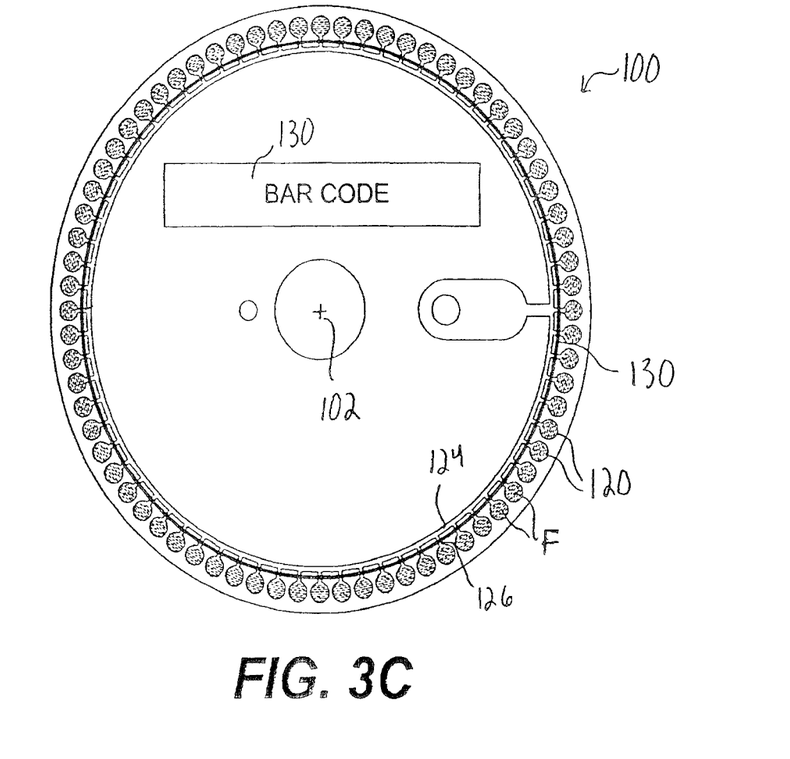
FIG. 3C is a plan view of the sample disk of FIG. 3B, after centrifugal loading of the test sample material into the sample chambers, and radial fill conduits in a blocked state.

After the sample S to be tested has been loaded into the sample chambers to join the already inserted reagents R to form final test material F, the sample disk may be staked. As shown in FIG. 3C, the radial fill conduits 126 may be staked, in one embodiment, by physically deforming portion 130 of the top layer of the sample disk in a manner similar to that performed on radial fill conduits 50 in the FIG. 1-2 embodiments. After the radial fill conduit is sufficiently blocked, the sample disk may be further rotated and thermally cycled. During or after thermal cycling, the optical characteristics of the final sample F may be detected by an optical detections system. In one embodiment, the optical detections system is similar to the LightCycler™ system of Roche Molecular Biochemicals.

As is clear from the above description, the present teachings may also include a method of centrifugally loading and thermally cycling a plurality of sample chambers on a sample disk.

It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. An apparatus for centrifugally loading and thermally cycling a sample disk, comprising:

a sample disk having at least one fill chamber, in fluid communication with at least one primary fill conduit, a plurality of circumferentially disposed first sample chambers comprising respective first openings, respective second openings and respective third openings and a plurality of circumferentially disposed second sample chambers, the second sample chambers comprising respective first openings and respective second openings, wherein the respective first openings are on a top surface of each respective second sample chamber and wherein the plurality of second sample chambers are configured to receive sample through respective first opening, and wherein the plurality of first sample chambers are the outermost disposed chambers on the sample disk; and a plurality of circumferential fill conduits positioned between and in fluid communication with adjacent first sample chambers and in fluid communication with the at least one primary fill conduit, a plurality of radial fill conduits, each radial fill conduit providing fluid communication between the respective third opening of one of the plurality of first sample chambers and the respective second opening of one of the plurality of second sample chambers, wherein the plurality of first sample chambers are centrifugally loaded with a first biological material from the fill chamber, subsequently further loaded with a second biological material from the plurality of circumferentially disposed second sample chambers, and thermally cycled.

2. The apparatus of claim 1, wherein the thermally cycling comprises a sample block thermally connected to the sample disk.

3. The apparatus of claim 2, wherein the thermally cycling further comprises a temperature control unit operatively connected to the sample block for raising and lowering the temperature of the sample block according to a user-defined profile.

4. An apparatus for centrifugally loading and thermally cycling a sample disk, comprising:

a sample disk having at least one fill chamber, in fluid communication with at least one primary fill conduit, a plurality of circumferentially disposed first sample chambers and a plurality of second circumferentially disposed sample chambers, and wherein the plurality of first sample chambers are the outermost disposed chambers on the sample disk and initially loaded with sample from the fill chamber;

a plurality of circumferential fill conduits positioned between and in fluid communication with adjacent first sample chambers and in fluid communication with the at least one primary fill conduit, a plurality of radial fill conduits, each radial fluid conduit positioned between and in fluid communication with a respective one of the plurality of first sample chambers and a respective one of the plurality of second sample chambers, each of the plurality of radial fill conduits configured to permit transfer of material from the respective one of the plurality of circumferentially disposed second sample chambers to the respective one of the plurality of first sample chambers upon rotation of the sample disk about a rotational axis; and a thermal cycler for thermally cycling the plurality of first sample chambers upon rotation of the sample disk about the rotational axis, wherein each second sample chamber is configured to permit introduction of material through a first opening on a top surface of each second sample chamber.

5. The apparatus of claim 4, wherein the thermal cycler comprises a sample block thermally connected to the sample disk.

6. The apparatus of claim 5, wherein the thermal cycler comprises a temperature control unit operatively connected to the sample block for raising and lowering the temperature of the sample block according to a user-defined profile.

7. The apparatus of claim 4, wherein the sample disk comprises a top layer and a bottom layer, wherein the bottom layer comprises a metal.

8. The apparatus of claim 7, wherein the top layer comprises polypropylene.

9. The apparatus of claim 4, wherein each of the plurality of first sample chambers has a volume of no more than 100 microliters.

10. The apparatus of claim 1, wherein the first openings each define a closable open aperture on the top surface of each of the plurality of first sample chambers.

11. The apparatus of claim 1, wherein the first sample chambers comprise respective second openings to fluidly communicate each first sample chamber with a respective second sample chamber.

12. The apparatus of claim 1, wherein at least one of the plurality of circumferentially disposed second sample chambers further comprise a top surface through which an optical detection system can detect the characteristics of sample materials in the second sample chambers.

13. The apparatus of claim 12, wherein each of the plurality of circumferentially disposed second sample chambers further comprise a top surface through which an optical detection system can detect the characteristics of sample materials in the second sample chambers.

14. The apparatus of claim 4, wherein at least one of the plurality of circumferentially disposed second sample chambers further comprise a top surface through which an optical detection system can detect the characteristics of sample materials in the second sample chambers.

15. The apparatus of claim 14, wherein each of the plurality of circumferentially disposed second sample chambers further comprise a top surface through which an optical detection system can detect the characteristics of sample materials in the second sample chambers.

16. The apparatus of claim 1, wherein the plurality of circumferentially disposed second sample chambers are PCR compatible.

17. The apparatus of claim 4, wherein the plurality of circumferentially disposed second sample chambers are PCR compatible.

* * * * *